(12) United States Patent
Eddy

(10) Patent No.: US 10,499,834 B2
(45) Date of Patent: Dec. 10, 2019

(54) PATIENT MOVEMENT NOTIFICATION DEVICE

(71) Applicant: Parasol Medical LLC, Buffalo Grove, IL (US)

(72) Inventor: Patrick E. Eddy, Allendale, MI (US)

(73) Assignee: Parasol Medical LLC, Buffalo Grove, IL (US)

( * ) Notice: Subject to any disclaimer, the term of this patent is extended or adjusted under 35 U.S.C. 154(b) by 626 days.

(21) Appl. No.: 14/171,319

(22) Filed: Feb. 3, 2014

(65) Prior Publication Data

US 2014/0221876 A1 Aug. 7, 2014

Related U.S. Application Data

(60) Provisional application No. 61/760,027, filed on Feb. 1, 2013.

(51) Int. Cl.
*A61B 5/00* (2006.01)
*A61B 5/11* (2006.01)

(52) U.S. Cl.
CPC .......... *A61B 5/1115* (2013.01); *A61B 5/1117* (2013.01); *A61B 5/6892* (2013.01); *A61B 5/7405* (2013.01)

(58) Field of Classification Search
CPC ... A61B 5/1115; A61B 5/1117; A61B 5/6892; A61B 2560/0412; A61B 5/7405
See application file for complete search history.

(56) References Cited

U.S. PATENT DOCUMENTS

| | | | | | |
|---|---|---|---|---|---|
| 4,551,028 | A | * | 11/1985 | Rowen | G04G 19/12 368/204 |
| 4,865,844 | A | * | 9/1989 | Blank | A61K 31/695 424/404 |
| 6,317,036 | B1 | * | 11/2001 | Popat | B62J 3/00 340/427 |
| 7,557,719 | B1 | * | 7/2009 | Long | A61B 5/1115 340/309.7 |

(Continued)

OTHER PUBLICATIONS

"TABS Mobility Monitor: User Instructions." Stanley Senior Technologies (2007): 1-25.*

(Continued)

*Primary Examiner* — Max F Hindenburg
(74) *Attorney, Agent, or Firm* — Price Heneveld LLP

(57) ABSTRACT

A patient movement notification device is provided that includes a sensor pad for sensing movement of a patient and generating a signal when movement of the patient is sensed, and an electronics module for generating a notification of patient movement in response to receipt of the signal from the sensor pad. The patient movement notification device may be disposable. Accordingly, the electronics module may permanently shut down to become non-functional a specified time period after activation. Further, the electronics module may include a housing including a slot; a contact terminal disposed in the housing; a battery disposed in the housing; and a tab extending between the battery and the contact terminal and extending out through the slot, wherein the tab prevents the electronics module from receiving power until such time as a user pulls the tab from the slot. The housing may be sealed to prevent access to the battery.

11 Claims, 2 Drawing Sheets

(56) References Cited

U.S. PATENT DOCUMENTS

| | | | | |
|---|---|---|---|---|
| 7,661,307 B1* | 2/2010 | Milone | | G01F 23/18 73/290 R |
| 7,916,036 B1* | 3/2011 | Pope | | G08B 21/02 200/85 A |
| 8,115,624 B2* | 2/2012 | Dayton | | G07C 3/00 340/539.14 |
| 2002/0067273 A1* | 6/2002 | Jaques | | A61B 5/11 340/573.4 |
| 2003/0120311 A1* | 6/2003 | Hansen | | A61N 1/39 607/5 |
| 2003/0216670 A1* | 11/2003 | Beggs | | A61B 5/1115 600/595 |
| 2004/0137959 A1* | 7/2004 | Salzhauer | | G08B 1/08 455/567 |
| 2008/0042835 A1* | 2/2008 | Russell | | A61B 5/1038 340/561 |
| 2008/0091089 A1* | 4/2008 | Guillory | | A61B 5/0478 600/301 |
| 2008/0278336 A1* | 11/2008 | Ortega | | A61B 5/1113 340/573.5 |
| 2010/0004715 A1* | 1/2010 | Fahey | | A61H 39/002 607/48 |
| 2010/0109879 A1* | 5/2010 | Hamdan | | A61B 5/1113 340/573.4 |
| 2011/0270179 A1* | 11/2011 | Ouyang | | A61B 1/00062 604/110 |
| 2013/0165809 A1* | 6/2013 | Abir | | A61B 5/1126 600/534 |

OTHER PUBLICATIONS

Isquith, A. J., E. A. Abbott, and P. A. Walters. "Surface-bonded antimicrobial activity of an organosilicon quaternary ammonium chloride." Applied microbiology 24.6 (1972): 859-863.*

* cited by examiner

Section A-A

PATIENT MOVEMENT NOTIFICATION DEVICE

CROSS-REFERENCE TO RELATED APPLICATION

This application claims priority to and the benefit under 35 U.S.C. § 119(e) of U.S. Provisional Patent Application No. 61/760,027, entitled "PATIENT MOVEMENT NOTIFICATION DEVICE," filed on Feb. 1, 2013 by Patrick E. Eddy, the entire disclosure of which is incorporated herein by reference.

BACKGROUND OF THE INVENTION

The present invention generally relates to a patient movement notification device, and more specifically relates to a patient movement notification device for preventing the patient from falling.

Patient movement notification devices serve to notify a patient's caretaker(s) who may better assist them. Such devices are used for patients who are at a high risk for fall related injury or for patients who are not healthy enough to stand (post-operative patients, etc.).

Patient movement notification devices are currently in use that include a disposable sensor that is positioned between the patient and a bed or chair, and an electronics module that connects to the sensor for generating an alarm when the patient removes pressure from the pad by getting out of bed or up from a chair. The alarm may be a recorded vocal command, such as "please stay in bed and use the nurse call button if you need assistance" or any other message that the caretaker may wish to record. Unlike the sensor portion, the electronics module is not disposable. The electronics module includes a plug receptacle for receiving the plug on the end of a cord that is permanently secured to the sensor.

Existing patient movement notification devices suffer from several drawbacks. The sensors are considered to be disposable and are typically only to be used for 15 days or less because the sensors are pressure sensitive and after having pressure continuously applied to the sensor, the sensor may not be able to re-expand when the patient removes pressure. However, hospitals have difficulty monitoring the times of use such that the sensors are often used well beyond the permitted 15 day lifetime. In addition, the electronics module component is considered a capital asset and therefore must be tracked and service must be performed on it once a year regardless of whether the module even needs service.

SUMMARY OF THE INVENTION

According to an embodiment of the present invention, a disposable patient movement notification device is provided comprising: a sensor pad for sensing movement of a patient and generating a signal when movement of the patient is sensed, and an electronics module electrically coupled to the sensor pad for generating a notification of patient movement in response to receipt of the signal from the sensor pad indicating movement of the patient, wherein the electronics module permanently shuts down to become non-functional a specified time period after activation.

According to another embodiment of the present invention, a disposable patient movement notification device is provided comprising: a sensor pad for sensing movement of a patient and generating a signal when movement of the patient is sensed, and an electronics module electrically coupled to the sensor pad for generating a notification of patient movement in response to receipt of the signal from the sensor pad indicating movement of the patient. The electronics module comprising: a housing including a slot opening into an interior of the housing; a battery contact terminal disposed in the housing; at least one battery disposed in the housing for powering the electronics module when a first end thereof is electrically coupled to the battery contact terminal; and a tab extending between the first end of the at least one battery and the battery contact terminal and extending out from the housing through the slot, wherein the tab prevents the electronics module from receiving power until such time as a user pulls the tab from the slot.

According to another embodiment of the present invention, a disposable patient movement notification device is provided comprising: a sensor pad for sensing movement of a patient and generating a signal when movement of the patient is sensed, and an electronics module electrically coupled to the sensor pad for generating a notification of patient movement in response to receipt of the signal from the sensor pad indicating movement of the patient. The electronics module comprising: a housing, and at least one battery disposed in the housing for powering the electronics module, wherein the housing is sealed so as to prevent access to the at least one battery.

According to another embodiment of the present invention, a sensor pad is provided for use in a patient movement notification device, the sensor pad comprising: a plastic sheet having conductive ink printed on a surface thereof to form two conductive contacts; two wires each secured to a respective one of the conductive contacts; a foam substrate provided over one of the conductive contacts, wherein the plastic sheet is folded and sealed such that the conductive contacts face one another with the foam substrate disposed therebetween.

According to another embodiment of the present invention, a patient movement notification device is provided comprising: a sensor pad for sensing movement of a patient and generating a signal when movement of the patient is sensed, and an electronics module electrically coupled to the sensor pad for generating a notification of patient movement in response to receipt of the signal from the sensor pad indicating movement of the patient, wherein the electronics module comprises a housing, wherein outer surfaces of at least one of the housing and the sensor pad are coated with an antimicrobial treatment, and wherein the antimicrobial treatment comprises a silane quaternary ammonium salt including an organofunctional silane covalently bonded to the outer surfaces.

According to another embodiment of the present invention, a patient movement notification device is provided comprising: a sensor pad for sensing movement of a patient and generating a signal when movement of the patient is sensed, and an electronics module. The electronics module comprising: a microphone for receiving audible notifications, converting the audio notifications into recorded audio signals; a memory for storing recorded audio signals received from the microphone; an audio amplifier for amplifying recorded audio signals received from the memory; a speaker for converting amplified recorded audio signals received from the audio amplifier into an audible notification; and a controller electrically coupled to the sensor pad, the memory, and the audio amplifier for causing recorded audio signals to be provided from the memory to the audio amplifier so as to generate an audible notification from the speaker in response to receipt of the signal from the sensor pad indicating movement of the patient, wherein the audio amplifier is powered down when not in use to minimize power draw.

According to another embodiment of the present invention, a patient movement notification device is provided comprising: a sensor pad for sensing movement of a patient and generating a signal when movement of the patient is sensed, and an electronics module. The electronics module comprising: a controller electrically coupled to the sensor pad, for providing a notification in response to receipt of the signal from the sensor pad indicating movement of the patient, wherein the controller sleeps in a low power consuming state and wakes up at regular intervals to poll user interface information and when a signal is received from the sensor pad.

These and other features, advantages, and objects of the present invention will be further understood and appreciated by those skilled in the art by reference to the following specification, claims, and appended drawings.

DETAILED DESCRIPTION OF PREFERRED EMBODIMENTS

Figure 1:
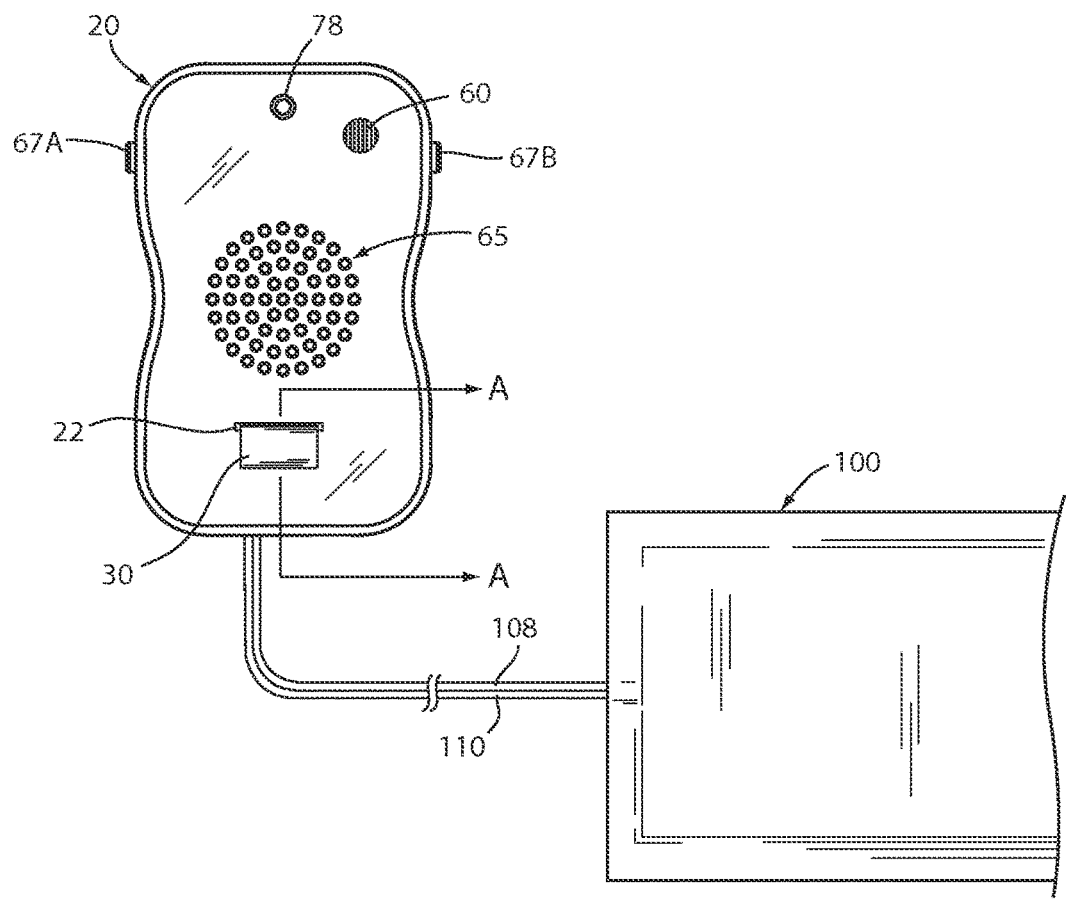
FIG. 1 is a partial isometric view of a patient movement notification device according to an embodiment of the present invention.

Reference will now be made in detail to the present preferred embodiments of the invention, examples of which are illustrated in the accompanying drawings. Wherever possible, the same reference numerals will be used throughout the drawings to refer to the same or like parts. In the drawings, the depicted structural elements are not to scale and certain components are enlarged relative to the other components for purposes of emphasis and understanding.

To address the problems with existing systems, an improved patient movement notification device is proposed whereby the electronics module is made in a manner so as to be disposable along with the sensor to which it is connected. This eliminates the need for monitoring this portion of the device as a capital asset. In addition, the electronics module may be constructed to permanently shut itself down to become non-functional a specified number of days after activation (i.e., 15 days from activation). In this way, the hospital can replace the sensors every 15 days as recommended by only checking if the device has shut down or is about to shut down rather than logging the dates of first use. In this regard, the electronics module may give an advance warning a few hours in advance and then shuts down. Because the device may be designed to relay the warning signal of patient movement to a nursing station, the device may further transmit the advance warning of shut down to the nursing station as well. It should be appreciated that the shut down (or time out) feature may be modified for non-disposable modules so that it provides a warning that the 15 day period is over or almost over.

Figure 1A:
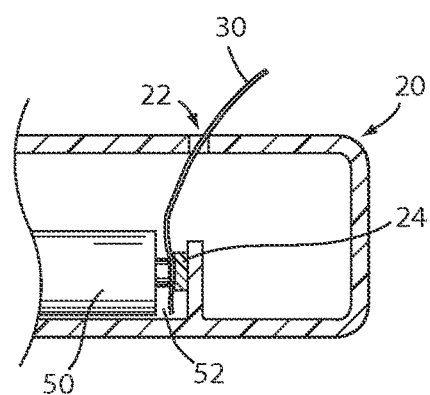
FIG. 1A is an elevational view of a cross section of a portion of the electronics module of the patient movement notification device shown in FIG. 1 taken along line A-A.
Figure 2:
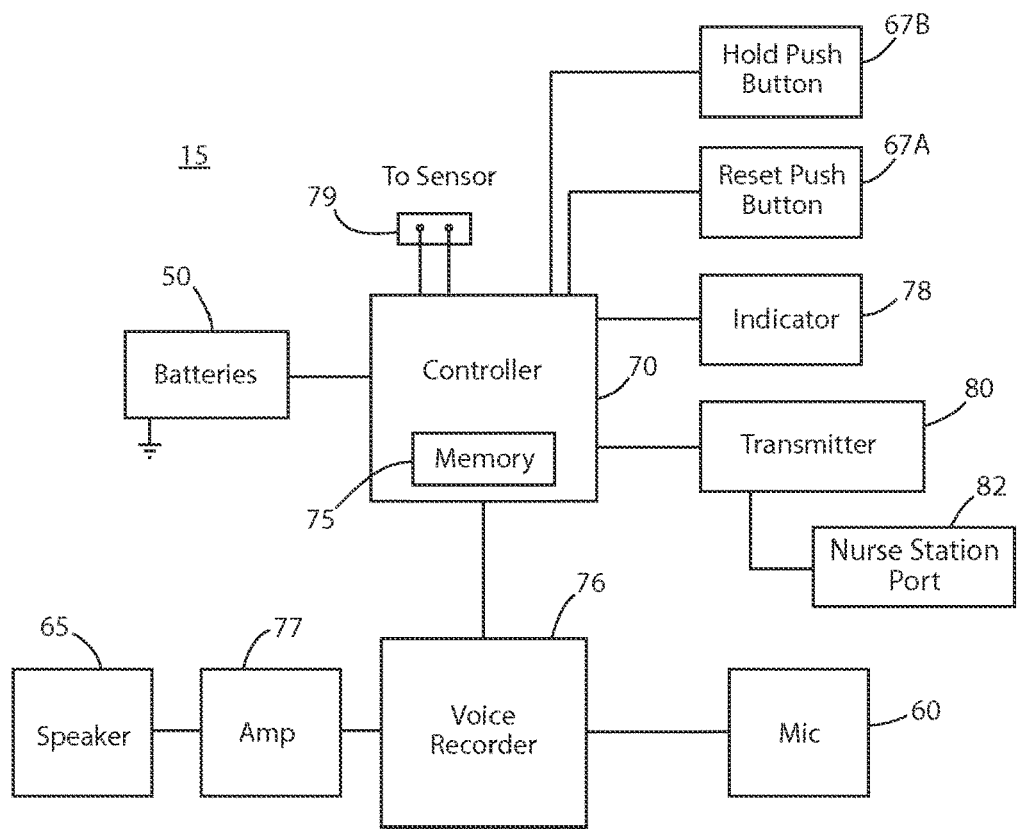
FIG. 2 is an electrical circuit diagram in block form of the electronics module of the patient movement notification device shown in FIG. 1.

The electronics module 15 may be configured as shown in FIG. 1 to include a housing 20 that may be in the size and form of a pendant or key fob. Housing 20 contains the electronics (described below) and a battery 50 (FIG. 2). Housing 20 is designed so that it does not allow access to the battery 50 such that it cannot be replaced or removed. This reduces parts count and cost of the unit and provides an inexpensive mechanism for activating the device as described further. Housing 20 further includes a slot 22 positioned proximate one end 52 of the battery 50 and a battery terminal 24 to which end 52 of battery 50 connects as shown in partial cross section in FIG. 1A. A plastic tab 30 is provided that extends from housing 20 through slot 22 and between end 52 of battery 50 and terminal 24 so as to prevent the electronics from receiving power until such time as a user pulls the tab 30 from slot 22.

The electronics that may be included in housing 20 are shown in FIG. 2. As shown, the device includes a connector 79 that may be a connector receptacle to receive a plug end of a wire extending from a sensor pad 100 or may be a permanent connection to the sensor pad 100.

The electronics may take any form capable of storing a voice recording, playing the voice recording back when detecting a signal from the sensor indicating movement of the patient, and shutting down or otherwise generating a warning signal a predetermined number of days following activation. As such, the electronics include a microphone 60, a speaker 65, a RESET push button 67A, a HOLD push button 67B, a controller 70 (which may be a microprocessor, digital signal processor, or discrete electronic components), memory 75 (which may be memory internal to a microprocessor), a voice recorder 76, an audio amplifier 77, a connector 79 for connecting to the sensor pad 100, and one or more batteries 50. In lieu of connector 79, the sensor pad 100 may be hardwired to electronics module 15, particularly if the electronics module 15 is to be disposed of with the sensor pad 100. The electronics may further include an LED indicator 78 and a transmitter/receiver 80 as further described below.

Figure 3:
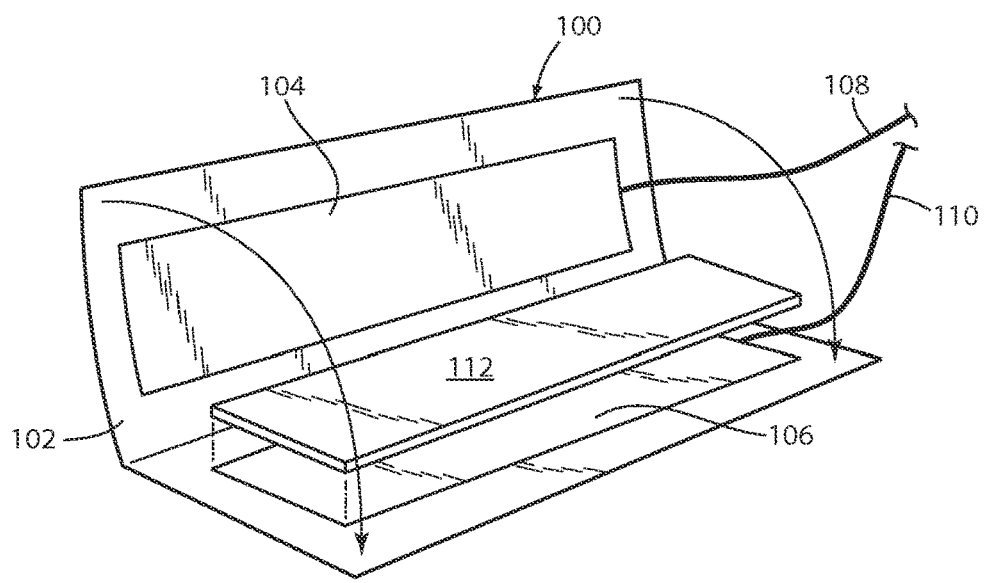
FIG. 3 is a perspective view of a sensor pad of the patient movement notification device shown in FIG. 1 shown in a partially assembled state.

The electronics module 15 may be used with conventional sensors or with a novel sensor pad 100 (FIG. 3). Current sensors pads are constructed using three pieces of cardboard, two of which are coated with conductive pads facing one another and a third piece of cardboard has foam attached and is placed in between the other two pieces of cardboard. A wire is attached to each conductive pad and then the sensor pad is sealed within a plastic pouch.

FIG. 3 shows an example of a novel sensor pad 100 whereby the inside surfaces of a plastic sheet 102 have conductive ink printed thereon to form conductive contacts 104 and 106. Wires 108 and 110 may then be secured to the conductive contacts 104, 106 and foam 112 may then be laid over one of the conductive contacts 104, 106. The plastic sheet 102 may then be folded and sealed such that the conductive contacts 104 and 106 face one another with foam 112 disposed therebetween. Such a sensor pad 100 may be formed in many different sizes and shapes. The novel sensor pad thus has fewer parts and lower cost.

Referring back to FIG. 2, optional transmitter 80 may be provided to transmit information (which may include alarms and other data) to a distant receiver that receives the information. This information may then be stored in an automated records database of the healthcare facility or otherwise provided at a nurse's station. The information may include any one or more of the following: warnings of a patient getting out of bed or out of a chair or wheelchair, the time and date of issuance of the warnings and the time and date the patient returned to bed or the chair, warnings of end of life approaching with a time and date stamp, and warning of end of life with a time and date stamp. The time and date stamps may be generated at the receiving side of the information and stored in the records database. Transmitter 80 may be coupled wirelessly or by wired connection such as USB. The records database may be a database such as a Cerner records database.

Transmitter 80 may be coupled wirelessly or by wired connection to a nursing station alarm switchboard so as to generate appropriate alarm signals at a nursing station that identifies the patient or room and the warnings so that the staff can take appropriate action. A connection port 82 may be provided for a wired connection to the nursing station.

In addition to providing the sensor on a bed, chair or wheelchair, another version of the sensor may be placed on a toilet to notify a caretaker that the patient has attempted to get up from the toilet on their own. A sensor for such a toilet application may be constructed using a flexible circuit that may be connected and adhered to a surface of the toilet that will contact the patient's skin. The device would thus sense the properties of human skin, not pressure. The unit activates once pressure is applied to the sensor or the patient touches the flex circuit contacts.

A low cost microcontroller may be used as controller 70 and may serve multiple purposes including: application logic; generating an alarm tone; coordinating the actions of other components; and capacitive touch and switch sensing. One suitable microcontroller is the PIC24F04KA200. It is an inexpensive entry level 16-bit controller in the PIC24 product catalogue from Microchip. The primary selection criteria for this particular controller are its integrated capacitive touch sensing hardware, its low cost and small form factor. The microcontroller operates at low voltages, nominally 3.0V, but is capable of operating while the battery level droops over its operating life (2.8 V).

The controller 70 is responsible for coordinating the actions of the device. Specifically, the controller 70 tracks the time that the unit is active (measured from initial power up). This time is cumulative and is stored periodically in non-volatile memory 75 (preventing tampering). When a pre-determined lifetime expires, the controller 70 no longer provides its basic operating functions. This requires the user to replace the unit.

The controller 70 does not have to actually record any sound data; however, it may control the state and operation of a voice recorder 76. Given user input (from the button 67 or the patient sensor), the controller 70 will command the voice recorder 76 to record or playback. The voice recorder 76 is solely responsible for handling the audio details.

Playback of a recording may also be performed by the voice recorder 76. The alarm tone that the unit may generate may be the controller's responsibility. This is done by simply toggling a pin that is connected to the audio line. This appears as a square wave to an audio amplifier 77, which in turn generates a loud alarm. The controller 70 controls the power up state of the audio amplifier 77. This is done to intelligently reduce power consumption during inactive periods. The controller turns the amplifier 77 on only when required.

Lastly, the controller 70 senses user input. The button 67 for recording is tracked by the controller 70. More importantly, the controller 70 contains all of the hardware for sensing patient contact with an attached flex circuit or patient sensor. The controller 70 may be programmed through a PGM connector.

The electronics module 15 may be configured to operate with either or both the flex circuit or pressure-sensitive sensor albeit different firmware may be needed. When used with a pressure-sensitive sensor, the CAP1/2 pins of the above-described microcontroller are shorted while the patient is seated. CAP1 is driven high while CAP2 is read. While the patient is seated, CAP2 will read high. When the switch is opened, R5 will pull CAP2 low, indicating an alarm condition. This configuration requires that R5 be populated with a high resistance (i.e., 100 kΩ-220 kΩ).

If patient sensing is done with a flex circuit with exposed metallic (or otherwise conductive) pads, the capacitance of the circuit is measured by alternately grounding and applying a constant current source to the sensor being measured. The time it takes to raise the sensor to a certain voltage is directly related to the capacitance of the circuit. Human tissue has a relatively high dielectric constant; enough to allow the unit to detect an easily measurable change in capacitance of the flex circuit when it is in contact with the patient.

For this configuration, R5 should be a 0Ω bridge or should be left open. While it is possible for the unit to function with R5 open, grounding the patient gives a more reliable reading.

Audio recording and playback may be handled by the voice recorder 76: the ISD1610B. This chip records audio data from an electrets microphone circuit. During playback, an audio signal is output from the ISD1610. This signal is routed to a sound amplifier which then drives an 8Ω speaker. The ISD1610 is capable of driving the speaker alone, however, the amplifier serves several functions: It amplifies the sound up to 1 W (more power than the ISD is capable of producing) and it allows the alarm tone to be generated by the controller 70.

The audio data may be sampled at 8 KHz. This affords up to 10 seconds of recording time. If the recording time should be longer, a slower sampling rate could be used (selectable by changing R9), or by selecting a different voice recorder in the ISD1600B series.

A TDA8541 audio amplifier may be used on the prototype device. It combines high audio output power with a shut-down feature that minimizes current draw during periods that the unit is idle. Because this is a battery powered application, this is a desirable. The TDA8541 is capable of up to 1 W audio output. In the configuration used on the prototype schematic, the maximum output is 0.68 W. This may be increased by changing the gain by modifying the ratio between R11 and R10. The gain produced by the TDA8541 is given by the equation:

$$G\_v = 2*R11/R10$$

The current configuration has a gain of 6 dB. If audio output volume is not acceptable, this gain factor may be increased up to 30 dB by changing the resistor ratio (R11 should be changed, while R10 should be left at about 11K).

Power may be drawn directly from one battery or two AA alkaline batteries connected in series to yield 3.0V. Although the direct connection to a battery with minimal regulation is not an elegant solution, it provides a solution with minimal cost. While the design may operate at 2.8V or down to 2.6V, batteries with a relatively flat discharge profile may be selected to maximize the reliability of the unit.

Because this is a battery operated device that is expected to last for a minimum of fifteen (15) days, batteries that are be capable of performing this long must be used. The above design is designed to minimize power draw in a sleep mode, greatly extending the lifetime of the unit. The audio amplifier 77 and voice recorder 76 may be powered down when not in use. Also, the controller 70 sleeps for the majority of its life, waking up at regular intervals to poll user interface information and when an alarm event occurs.

The outer surfaces of housing 20 and sensor pad 100 are preferably treated with an antimicrobial substance. The surfaces of housing 20 and sensor 100 are coated with an antimicrobial treatment that may be sprayed onto the surfaces using a solution and/or may be applied using wipes soaked in such a solution. Suitable wipes and solutions are disclosed in commonly-assigned U.S. Pat. No. 8,491,922, the entire disclosure of which is incorporated herein by reference.

In a preferred form, the antimicrobial treatment solution contains 30-50 percent isopropyl alcohol and 50-70 percent antimicrobial treatment substance, which is preferably a silane quaternary ammonium salt having an unreacted organofunctional silane. If the antimicrobial treatment solution is applied by spraying, the solution most preferably includes 50 percent isopropyl alcohol and 50 percent of the unreacted antimicrobial treatment substance. If the solution is applied using the wipes, the solution is preferably 30 percent isopropyl alcohol and 70 percent of the unreacted antimicrobial treatment substance.

The preferred silane quaternary ammonium salt includes an active ingredient of 3-(trimethoxysilyl) propyldimethyloctadecyl ammonium chloride and other inert ingredients. The silane quaternary ammonium salt preferably includes about 0.1 to 50 percent of the 3-(trimethoxysilyl) propyldimethyloctadecyl ammonium chloride and most preferably includes about 5 percent of the 3-(trimethoxysilyl) propyldimethyloctadecyl ammonium chloride. Such silane quaternary ammonium salts are available from Aegis Environments, of Midland, Mich., which is identified as "AEM 5772-5 Antimicrobial," and from Piedmont Chemical Industries I, LLC of High Point, N.C., which is identified as "PROMOFRESH X 105." The antimicrobial treatment solution with the isopropyl alcohol is available from MicrobeCare, LLC of Allendale, Mich., under the trademark MICROBECARE™.

The isopropyl alcohol may have a concentration of 70-90 percent. By providing the unreacted organofunctional silane in isopropyl alcohol, the organofunctional silane does not react with the wipe substrates or the inside of the wipe container such that it is free to later react and permanently covalently bond with the surfaces of housing 20 and sensor Pad 100. Isopropyl alcohol is preferred as it evaporates quickly once the solution is wiped onto the treated surface to allow the unreacted organofunctional silane to more quickly react with the treated surface.

The above described silane quaternary ammonium salt is preferred because it is an organofunctional silane antimicrobial treatment substance that is substantially free from arsenic, silver, tin, heavy metals and polychlorinated phenols; copper; or a silver-ion emitter. In addition, it not only eliminates bacteria on contact, but it remains on the treated surfaces and kills any bacteria subsequently contacting these surfaces. Such treatment preferably lasts at least one week, more preferably several months, and most preferably indefinitely.

The preferred organofunctional silane also prevents odor, staining and product deterioration that may be associated with microbe contamination. The preferred organofunctional silane is also beneficial because it permanently bonds to a treated surface, covers a broad spectrum of activity with no negative effects or drawbacks, and is easily incorporated and easily verifiable.

The preferred organofunctional silane is designed to react and create a covalent bond with the surfaces of housing 20 and sensor 100. The reacted substance is held onto those surfaces until the covalent bond is broken. Tests have shown that most industrial cleaners or disinfectants will not remove the preferred antimicrobial treatment substance. The method of removal is by abrasion.

Although particular antimicrobial substances are disclosed, any antimicrobial substance may be used. Examples of some other forms of antimicrobial substances include a substance that emits silver-ions, such as a plastic co-molded or co-extruded with a silver-ion emitter (like MCX 122656, manufactured by RTP Co., Winona, Minn.), or a plastic coated or plated with a silver-ion emitter. As other examples, the antimicrobial substance hyaluronan and its derivatives, and triclosan. The emission of ions from substances such as the aforementioned aid in the destruction of microbes on a cellular level. Such ions need not necessarily be silver ions. Still other examples include AEGIS Microbe Shield™ (from Aegis Environments, Midland, Mich.), which is a copolymer of chloropropyltrihydroxysilane and octadecylaminodimethyltrihydroxysilylpropyl ammonium chloride. Other examples of suitable antimicrobial substances include Microguard® (by Microguard, Olivet, France), which is liquid solution containing hydrophilic polymers, and Microban® antimicrobial plastic additive available from Microban International. Other antimicrobial substances include an organosilicon antimicrobial that is substantially free from arsenic, silver, tin, heavy metals and polychlorinated phenols. The antimicrobial substance could be copper or a silver-ion emitter. One silver-ion emitter is GermGate™ (from Bovie Screen Process Co., Inc., Bow, N.H.), which is a nano particle silver based, liquid coating that can be coated onto a fabric. Another silver-ion emitter is ProtexAG (from Carolina Silver Technologies, North Carolina), which is silver-based coating that can be coated onto fabric. Yet other silver-ion emitting coatings are those available from Covalon Technologies, Ltd. of Mississauga, Ontario, Canada and Agion® antimicrobial coating available from Agion Technologies Ltd. of Wakefield, Mass. In addition, silver sodium hydrogen zirconium phosphate may be used as the antimicrobial substance. In general terms, an antimicrobial substance is capable of emitting ions that aid in the destruction of a microbe.

Alternate antimicrobial materials may be used that are tolerant of appropriate cleaning and sterility methods. An example of which is zirconium phosphate such as Model No. XDK801 available from Xiamen Xindakang Inorganic Materials Co., Ltd. and Zeolite carrying silver, Model No. XDK101 available from Xiamen Xindakang Inorganic Materials Co., Ltd.

The above description is considered that of the preferred embodiments only. Modifications of the invention will occur to those skilled in the art and to those who make or use the invention. Therefore, it is understood that the embodiments shown in the drawings and described above are merely for illustrative purposes and not intended to limit the scope of the invention, which is defined by any subsequently presented claims as interpreted according to the principles of patent law, including the doctrine of equivalents.

What is claimed is:

1. A disposable patient movement notification device, comprising:

a sensor pad for sensing movement of a patient and generating a signal when movement of the patient is sensed; and an electronics module electrically coupled to said sensor pad for generating a notification of patient movement in response to receipt of the signal from said sensor pad indicating movement of the patient, wherein said electronics module permanently shuts down to become non-functional a specified time period after activation, wherein said electronics module generates an advance shutdown warning signal in advance of shutting down and transmits the advance shutdown warning signal to a nursing station.

2. The disposable patient movement notification device of claim 1, wherein said electronics module further comprises:
a housing; and
at least one battery disposed in said housing for powering the electronics module,
wherein said housing is sealed so as to prevent access to said at least one battery.

3. The patient movement notification device of claim 1, wherein said electronics module further comprises:
a housing including a slot opening into an interior of said housing;
a battery contact terminal disposed in said housing;
at least one battery disposed in said housing for powering the electronics module when a first end thereof is electrically coupled to said battery contact terminal; and
a tab extending between the first end of said at least one battery and said battery contact terminal and extending out from said housing through said slot, wherein said tab prevents said electronics module from receiving power until such time that a user pulls said tab from said slot.

4. The disposable patient movement notification device of claim 1, wherein said sensor pad comprises:
a plastic sheet having conductive ink printed on a surface thereof to form two conductive contacts;
two wires each secured to a respective one of said conductive contacts, wherein said wires provide an electrical coupling to said electronics module;
a foam provided over one of said conductive contacts,
wherein said plastic sheet is folded and sealed such that said conductive contacts face one another with said foam disposed therebetween.

5. The disposable patient movement notification device of claim 1, wherein said electronics module comprises a housing, wherein outer surfaces of at least one of said housing and said sensor pad are coated with an antimicrobial treatment, and wherein said antimicrobial treatment comprises a silane quaternary ammonium salt including an organofunctional silane for covalently bonding to said outer surfaces.

6. The disposable patient movement notification device of claim 1, wherein the specified time period is 15 days.

7. The disposable patient movement notification device of claim 1, wherein said electronics module comprises:

a microphone for receiving audible notifications, converting the audio notifications into recorded audio signals;
a memory for storing recorded audio signals received from said microphone;
an audio amplifier for amplifying recorded audio signals received from said memory;
a speaker for converting amplified recorded audio signals received from said audio amplifier into an audible notification; and
a controller electrically coupled to said sensor pad, said memory, and said audio amplifier for causing recorded audio signals to be provided from said memory to said audio amplifier so as to generate an audible notification from said speaker in response to receipt of the signal from said sensor pad indicating movement of the patient.

8. The disposable patient movement notification device of claim 7, wherein said audio amplifier is powered down when not in use to minimize power draw.

9. The disposable patient movement notification device of claim 7, wherein said controller sleeps in a low power consuming state and wakes up at regular intervals to poll user interface information and when a signal is received from said sensor pad.

10. The disposable patient movement notification device of claim 1, wherein said electronics module comprises a controller electrically coupled to said sensor pad configured to coordinate actions of the electronics module, track the time that the electronics module is active, and permanently shut down the electronics module to become non-functional the specified time period after activation.

11. The disposable patient movement notification device of claim 1, wherein said electronics module comprises:
a housing including a slot opening into an interior of said housing;
a battery contact terminal disposed in said housing;
at least one battery disposed in said housing for powering the electronics module when a first end thereof is electrically coupled to said battery contact terminal; and
a tab extending between the first end of said at least one battery and said battery contact terminal and extending out from said housing through said slot, wherein said tab prevents said electronics module from receiving power until such time that a user pulls said tab from said slot,
wherein said housing is sealed so as to prevent access to said at least one battery; and
a controller electrically coupled to said sensor pad configured to coordinate actions of the electronics module, track the time that the electronics module is active, and permanently shut down the electronics module to become non-functional the specified time period after the time that a user pulls said tab from said slot to activate the electronics module.

* * * * *